United States Patent
Evans et al.

(10) Patent No.: US 10,751,686 B2
(45) Date of Patent: Aug. 25, 2020

(54) METHOD FOR PREPARING A SORBENT

(71) Applicant: JOHNSON MATTHEY PUBLIC LIMITED COMPANY, London (GB)

(72) Inventors: Matthew James Evans, Cleveland (GB); Matthew David Gwydion Lunn, Cleveland (GB); Martin Graham Partridge, Cleveland (GB); Christopher John Young, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 244 days.

(21) Appl. No.: 15/578,502

(22) PCT Filed: May 5, 2016

(86) PCT No.: PCT/GB2016/051279
§ 371 (c)(1),
(2) Date: Nov. 30, 2017

(87) PCT Pub. No.: WO2016/193659
PCT Pub. Date: Dec. 8, 2016

(65) Prior Publication Data
US 2018/0161752 A1 Jun. 14, 2018

(30) Foreign Application Priority Data
Jun. 5, 2015 (GB) .................... 1509822.1

(51) Int. Cl.
*B01J 20/02* (2006.01)
*B01J 20/08* (2006.01)
*B01J 20/30* (2006.01)
*B01J 20/28* (2006.01)
*C10G 25/00* (2006.01)
*B01D 15/00* (2006.01)
*C10L 3/10* (2006.01)
*B01D 15/08* (2006.01)
*C01B 3/56* (2006.01)
*C07C 7/12* (2006.01)
*C11B 3/10* (2006.01)
*B01D 53/04* (2006.01)

(52) U.S. Cl.
CPC .......... *B01J 20/0285* (2013.01); *B01D 15/00* (2013.01); *B01D 15/08* (2013.01); *B01D 53/04* (2013.01); *B01J 20/0237* (2013.01); *B01J 20/08* (2013.01); *B01J 20/2803* (2013.01); *B01J 20/28004* (2013.01); *B01J 20/28011* (2013.01); *B01J 20/28061* (2013.01); *B01J 20/3007* (2013.01); *B01J 20/3028* (2013.01); *B01J 20/3042* (2013.01); *B01J 20/3078* (2013.01); *C01B 3/56* (2013.01); *C07C 7/12* (2013.01); *C10G 25/003* (2013.01); *C10L 3/101* (2013.01); *B01D 2253/1128* (2013.01); *B01D 2253/304* (2013.01); *B01D 2253/306* (2013.01); *B01D 2257/602* (2013.01); *B01J 2220/42* (2013.01); *C01B 2203/042* (2013.01); *C10G 2300/202* (2013.01); *C10L 2290/542* (2013.01); *C11B 3/10* (2013.01)

(58) Field of Classification Search
CPC ........ B01J 20/02; B01J 20/08; B01J 20/0285; B01J 20/0237; B01J 20/0233; B01J 20/28; B01J 20/28002; B01J 20/28004; B01J 20/28011; B01J 20/28016; B01J 20/28019; B01J 20/2803; B01J 20/28057; B01J 20/28061; B01J 20/3007; B01J 20/30; B01J 20/3028; B01J 20/3042; B01J 20/3078; B01D 15/00; B01D 15/08; B01D 53/04; B01D 2253/10; B01D 2253/104; B01D 2253/112; B01D 2253/1122; B01D 2253/1128; B01D 2253/302; B01D 2253/306; B01D 2257/60; B01D 2257/602; C07C 7/12; C10G 25/003
See application file for complete search history.

(56) References Cited

U.S. PATENT DOCUMENTS

| | | | |
|---|---|---|---|
| 2,915,365 A | 12/1959 | Saussol | |
| 3,226,191 A | 12/1965 | Osment | |
| 4,094,777 A * | 6/1978 | Sugier | B01D 15/00 210/670 |
| 4,902,662 A * | 2/1990 | Toulhoat | B01D 53/64 502/216 |
| 4,909,926 A * | 3/1990 | Yan | C10G 25/00 208/251 R |

(Continued)

FOREIGN PATENT DOCUMENTS

| CN | 102046269 A | 5/2011 |
|---|---|---|
| CN | 104105536 A | 10/2014 |

(Continued)

OTHER PUBLICATIONS

T.Ohtani, et al., "Synthesis of Binary Copper Chalcogenides by Mechanical Alloying," Materials Research Bulletin, vol. 30, No. 12, pp. 1495-1504, 1995.

(Continued)

Primary Examiner — Katherine Zalasky McDonald
(74) Attorney, Agent, or Firm — BakerHostetler

(57) ABSTRACT

A method is described for preparing a sorbent comprising the steps of: (i) mixing together a particulate copper sulphide material and a particulate calcined rehydratable alumina, (ii) shaping the mixture, and (iii) drying the shaped mixture to form a dried sorbent.

20 Claims, No Drawings

(56) References Cited

U.S. PATENT DOCUMENTS

| | | | | |
|---|---|---|---|---|
| 5,024,683 | A * | 6/1991 | Tooley | B01D 53/02 95/141 |
| 5,120,515 | A | 6/1992 | Audeh et al. | |
| 5,190,908 | A * | 3/1993 | Audeh | B01D 53/02 423/210 |
| 5,223,145 | A * | 6/1993 | Markovs | B01D 15/00 210/673 |
| 5,245,106 | A * | 9/1993 | Cameron | B01D 53/64 423/215.5 |
| 5,401,393 | A * | 3/1995 | Whitehurst | C10G 25/02 208/251 R |
| 5,948,726 | A * | 9/1999 | Moskovitz | B01D 53/02 423/604 |
| 5,955,393 | A * | 9/1999 | Moskovitz | B01D 53/02 204/157.44 |
| 5,985,790 | A * | 11/1999 | Moskovitz | B01J 20/06 423/604 |
| 2001/0009884 | A1* | 7/2001 | Moskovitz | B01D 53/02 502/263 |
| 2007/0037991 | A1* | 2/2007 | Rizkalla | B01J 21/04 549/533 |
| 2007/0122327 | A1 | 5/2007 | Yang et al. | |
| 2009/0155148 | A1* | 6/2009 | Kanazirev | C10G 25/003 423/210 |
| 2009/0297885 | A1* | 12/2009 | Gadkaree | B01D 53/02 428/698 |
| 2010/0320153 | A1* | 12/2010 | Cousins | B01J 20/0237 210/688 |
| 2013/0053234 | A1* | 2/2013 | Fish | B01D 53/64 502/10 |
| 2013/0202503 | A1 | 8/2013 | Simonetti et al. | |
| 2014/0155260 | A1 | 6/2014 | Turbeville et al. | |

FOREIGN PATENT DOCUMENTS

| | | |
|---|---|---|
| GB | 1042158 A1 | 9/1966 |
| WO | WO2009101429 A1 | 8/2009 |
| WO | 2009145877 A1 | 12/2009 |
| WO | N02010061212 A1 | 6/2010 |
| WO | NO2011021024 A1 | 2/2011 |
| WO | WO2011081836 A2 | 7/2011 |
| WO | 2013119357 A1 | 8/2013 |
| WO | WO2014016560 A1 | 1/2014 |
| WO | WO2014016561 A1 | 1/2014 |
| WO | WO2015015068 A1 | 2/2015 |
| WO | N02015092358 A1 | 6/2015 |
| WO | N02015092359 A1 | 6/2015 |

OTHER PUBLICATIONS

GB1607835.4, Combined Search and Examination Report under Section 17 and 18(3) dated Dec. 6, 2016.
GB1509822.1, Search Report under Section 17(5) dated Dec. 14, 2015.
PCT/GB2016/051279, International Search Report dated Jul. 18, 2016.
PCT/GB2016/051279, Written Opinion dated Jul. 18, 2016.
PCT/GB2016/051281, Written Opinion dated Aug. 5, 2016.
PCT/GB2016/051280, Written Opinion dated Aug. 5, 2016.

* cited by examiner

METHOD FOR PREPARING A SORBENT

CROSS-REFERENCE TO RELATED APPLICATIONS

This application is the National Stage of International Patent Application No. PCT/GB2016/051279 filed May 5, 2016, which claims priority from Great Britain Patent Application No. 1509822.1, filed June 5, 2015, the disclosures of each of which are incorporated herein by reference in their entirety.

This invention relates to a method for preparing a sorbent, in particular a method for preparing sorbents comprising copper sulphide.

Copper sulphide containing sorbents are useful in removing heavy metals from fluid streams. Heavy metals such as mercury are found in small quantities in fluid streams such as hydrocarbon or other gas and liquid streams. Arsenic and antimony may also be found in small quantities in hydrocarbon streams. Mercury, in addition to its toxicity, can cause failure of aluminium heat exchangers and other processing equipment. Therefore there is a need to efficiently remove these metals from fluid streams, preferably as early as possible in the process flowsheet.

Copper sulphide is conventionally formed in the sorbents either in situ by reaction of a sorbent precursor containing a sulphidable copper compound with hydrogen sulphide ($H_2S$) present in the fluid stream, or by pre-sulphiding the sorbent precursor again with hydrogen sulphide. This reaction is depicted for copper oxide as follows:

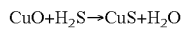

$$CuO + H_2S \rightarrow CuS + H_2O$$

Similarly, where copper hydroxycarbonate materials are used, both $CO_2$ and $H_2O$ are evolved.

WO2009/101429 discloses a method for making an absorbent comprising the steps of: (i) forming a composition comprising a particulate copper compound capable of forming copper sulphide, a particulate support material, and one or more binders, (ii) shaping the composition to form an absorbent precursor, (iii) drying the absorbent precursor material, and (iv) sulphiding the precursor to form the absorbent. The sulphiding agent used to sulphide the absorbent precursor may be one or more sulphur compounds such as hydrogen sulphide, carbonyl sulphide, mercaptans and polysulphides, or mixtures of these. Hydrogen sulphide is preferred.

It was believed that the conversion of the copper compounds was necessary in order to provide a sorbent with suitable physical properties and effective capacity for heavy metals. However, the sulphiding method using these sulphiding agents if not carefully controlled can lead to in-homogeneous product and impaired physical properties. Moreover hydrogen sulphide is a toxic gas and control measures are necessary for sulphiding at large scale. Therefore there is a need to seek alternative methods that are inherently safer, simpler and offer improved product homogeneity.

There is also a need to improve the product physical properties, notably the crush strength, which presently relies on the use of one or more binders.

We have found that replacing the particulate support material and binder combination with a particulate calcined, rehydratable alumina improves the sorbent properties.

Accordingly the invention provides a method for preparing a sorbent comprising the steps of:
(i) mixing together a particulate copper sulphide material and a particulate calcined, rehydratable alumina,
(ii) shaping the mixture, and
(iii) drying the shaped mixture to form a dried sorbent.

The invention further provides a sorbent obtainable by the method and the use of the sorbent in removing heavy metals such as mercury, arsenic selenium, cadmium and antimony, from heavy metal-containing fluid streams.

By "sorbent" we include absorbent and adsorbent.

By "calcined, rehydratable alumina" we mean a calcined amorphous or poorly crystalline transition alumina comprising one or more of rho-, chi- and pseudo gamma-aluminas. Such aluminas are capable of rehydration and can retain substantial amounts of water in a reactive form. Calcined, rehydratable aluminas are commercially available, for example as "CP alumina powders" available from BASF AG. They may be prepared, for example, by milling gibbsite ($Al(OH)_3$), to a 1-20 micron particle size followed by flash calcination for a short contact time as described in U.S. Pat. No. 2,915,365. In addition to gibbsite, amorphous aluminum hydroxide and other naturally found mineral crystalline hydroxides such as Bayerite and Nordstrandite or monoxide hydroxides, such as Boehmite (AlOOH) and Diaspore may be also used as a source of the calcined, rehydratable alumina.

The particulate copper sulphide used to prepare the sorbent may be sourced commercially or may be prepared by a number of methods. Suitable methods include roasting of copper or a copper compound with elemental sulphur, solvothermal processes, hydrothermal processes (e.g. microwave irradiation), electrodeposition techniques, precipitation of copper sulphide from solution, sulphiding of copper compounds using hydrogen sulphide, electron irradiation or by a mechanochemical process in which powdered copper metal is mixed with elemental sulphur under conditions that cause the elemental copper and elemental sulphur to react to form one or more copper sulphides. Such methods are described in the *Materials Research Bulletin*, vol 30, no 12, p 1495-1504, 1995.

Copper sulphides that may be used include Copper (II) sulphide, CuS, (covellite) and/or substoichiometric copper sulphides, e.g. of formula $Cu_{2-x}S$ where x is 0-1, such as $Cu_9S_5$ (digenite). One or more copper sulphides may be used. Copper sulphides high in CuS are preferred, and the overall S:Cu atomic ratio of the particulate copper sulphide is preferably 0.8, more preferably 0.9, most preferably 0.95. Desirably, essentially all of the sulphided copper in the sorbent is in the form of copper (II) sulphide, CuS. The particulate copper sulphide may be in the form of a powder, preferably a powder with an average particle size, i.e. $D_{50}$, in the range 5-100 μm.

The dried sorbent may comprise 5-75% by weight, preferably 10-75% by weight, more preferably 15-55% by weight, especially 15-50% by weight, of copper sulphide (expressed as CuS).

The particulate calcined, rehydratable alumina is preferably an amorphous or poorly crystalline transition alumina comprising one or more of rho-alumina, chi-alumina and pseudo-gamma alumina. Preferably the particulate calcined, rehydratable alumina consists of one or more of rho-alumina, chi-alumina and pseudo-gamma alumina, especially rho-alumina. The particulate calcined, rehydratable alumina is desirably in the form of a powder, more preferably a powder with a $D_{50}$ particle size in the range 1-100 μm, preferably 1-20 μm, especially 1-10 μm. The BET Surface area of the calcined, rehydratable alumina as determined by nitrogen adsorption may be in the range 200-400 m²/g, preferably 250-300 m²/g.

The dried sorbent may comprise 25-95% by weight, preferably 25-90% by weight, of the particulate calcined, rehydratable alumina.

We have found that no other additives are necessary and therefore that the first step in the method for preparing the sorbent may comprise forming a mixture consisting of the particulate copper sulphide and the particulate calcined, rehydratable alumina.

One or more clay binders and/or cement binders may be included but these are not necessary.

In a preferred embodiment, binders are not included, in which case the sorbent may be considered to be "binderless".

In a preferred embodiment, the sorbent consists essentially of copper sulphide and the particulate calcined, rehydratable alumina.

The mixture comprising copper sulphide and particulate calcined, rehydratable alumina is shaped and dried to form the sorbent. Shaping may be by pelleting, extruding or granulating. Hence, sorbent pellets may be formed by moulding a powder composition, generally containing a material such as graphite or magnesium stearate as a moulding aid, in suitably sized moulds, e.g. as in conventional tableting operation. Alternatively, sorbent extrudates may be formed by forcing a suitable composition and often a little water and/or a moulding aid as indicated above, through a die followed by cutting the material emerging from the die into short lengths. For example extrudates may be made using a pellet mill of the type used for pelleting animal feedstuffs, wherein the mixture to be pelleted is charged to a rotating perforate cylinder through the perforations of which the mixture is forced by a bar or roller within the cylinder: the resulting extruded mixture is cut from the surface of the rotating cylinder by a doctor knife positioned to give extruded pellets of the desired length. Alternatively, sorbent granules, in the form of agglomerates, may be formed by mixing a powder composition with a little liquid, such as water, insufficient to form a slurry, and then causing the composition to agglomerate into roughly spherical granules in a granulator. The amount of liquid added will vary depending upon the porosity and wettability of the components, but may be 0.1 to 0.5 ml/g of support mixture. Aqueous or non-aqueous liquids may be used, but water is preferred. Minimizing the amount of liquid used advantageously reduces the drying time of the sorbent and may reduce the formation of undesirable copper sulphates. Similarly, granulating the mixture under a non-oxidising atmosphere, such as oxygen-free nitrogen, reduces the potential formation of sulphates. Suitable granulator equipment is available commercially. The liquid may be conveniently added by spraying.

The pellets, extrudates or granules preferably have a length and width in the range 1 to 25 mm, with an aspect ratio (longest dimension divided by shortest dimension) 4.

The different shaping methods have an effect on the surface area, porosity and pore structure within the shaped articles and in turn this often has a significant effect on the sorption characteristics and on the bulk density. Thus beds of sorbents in the form of moulded pellets may exhibit a relatively broad absorption front, whereas beds of granulated agglomerates can have a much sharper absorption front: this enables a closer approach to be made to the theoretical absorption capacity. On the other hand, agglomerates generally have lower bulk densities than tableted compositions. Furthermore, in view of the presence of copper sulphide, methods involving small amounts of water are preferred to avoid possible sulphate formation, which is undesirable. Accordingly, it is preferred to make the shaped units in the form of agglomerates and thus a preferred shaping method involves granulating the mixture of copper sulphide and calcined, rehydratable alumina in a granulator. Granules with a diameter in the range 1-15 mm are preferred. The amount of water used in granulating the mixtures has been found to have an influence on the strength of the resulting granules. The amount of water used in the granulation may be in the range 0.25 ml/g of powder to 0.6 ml/g of the mixture of copper sulphide and calcined, rehydratable alumina. This is higher than the prior art granulated products that typically require <0.2 ml/g of mixture and arises from the unusual properties of the calcined, rehydratable alumina.

The shaped absorbent may be aged to enhance its strength before drying. Ageing of the calcined, rehydratable alumina-containing sorbents is suitably performed at 20-90° C., preferably 40-90° C. An advantage of using just the calcined, rehydratable alumina in the sorbent is that the ageing step may be considerably reduced or eliminated compared to prior art materials. Thus ageing may be performed on calcined, rehydratable alumina containing granules for 0.5-8 hours, preferably 0.5-6 hours, more preferably 0.5-2 hours before drying. Ageing under a non-oxidising atmosphere such as dry nitrogen reduces the potential for sulphate formation.

The shaped sorbent is dried. Conventional drying equipment may be used. Drying temperatures up to 120° C. may be used. Drying times may be in the range 0.25-16 hours. Drying under a non-oxidising atmosphere such as dry nitrogen reduces the potential for sulphate formation.

The sorbent may be used to treat both liquid and gaseous fluid streams containing heavy metals, in particular fluids containing mercury and/or arsenic. In one embodiment, the fluid stream is a hydrocarbon stream. The hydrocarbon stream may be a refinery hydrocarbon stream such as naphtha (e.g. containing hydrocarbons having 5 or more carbon atoms and a final atmospheric pressure boiling point of up to 204° C.), middle distillate or atmospheric gas oil (e.g. having an atmospheric pressure boiling point range of 177° C. to 343° C.), vacuum gas oil (e.g. atmospheric pressure boiling point range 343° C. to 566° C.), or residuum (atmospheric pressure boiling point above 566° C.), or a hydrocarbon stream produced from such a feedstock by e.g. catalytic reforming. Refinery hydrocarbon steams also include carrier streams such as "cycle oil" as used in FCC processes and hydrocarbons used in solvent extraction. The hydrocarbon stream may also be a crude oil stream, particularly when the crude oil is relatively light, or a synthetic crude stream as produced from tar oil or coal extraction for example. Gaseous hydrocarbons may be treated using the process of the invention, e.g. natural gas or refined paraffins or olefins, for example. Off-shore crude oil and off-shore natural gas streams in particular may be treated with the sorbent. Contaminated fuels such as petrol or diesel may also be treated. Alternatively, the hydrocarbon may be a condensate such as natural gas liquid (NGL) or liquefied petroleum gas (LPG), or gases such as a coal bed methane, landfill gas or biogas. Gaseous hydrocarbons, such as natural gas and associated gas are preferred.

Non-hydrocarbon fluid streams which may be treated include carbon dioxide, which may be used in enhanced oil recovery processes or in carbon capture and storage, solvents for decaffeination of coffee, flavour and fragrance extraction, solvent extraction of coal etc. Fluids, such as alcohols (including glycols) and ethers used in wash processes or drying processes (e.g. triethylene glycol, monoethylene glycol, Rectisol™, Purisol™ and methanol), may be treated by the inventive process. Mercury may also be removed from amine streams used in acid gas removal units. Natural oils and fats such as vegetable and fish oils may be treated, optionally after further processing such as hydrogenation or transesterification e.g. to form biodiesel.

Other fluid streams that may be treated include the regeneration gases from dehydration units, such as molecular sieve off-gases, or gases from the regeneration of glycol driers. The sorbent is of utility where the fluid stream contains water, preferably in low levels in the range 0.02 to 1% vol. Higher levels up to 5% vol may be tolerated for short periods. The sorbents may be regenerated simply after prolonged exposure to water simply by purging with a dry gas, preferably a dry inert gas such as nitrogen.

Preferably the sorption of heavy metal is conducted at a temperature below 150° C., preferably at or below 120° C. in that at such temperatures the overall capacity for heavy metal absorption is increased. Temperatures as low as 4° C. may be used. A preferred temperature range is 10 to 60° C. The gas hourly space velocity through the sorbent may be in the range normally employed.

Furthermore, the sorbent may be used to treat both liquid and gaseous fluid streams containing one or more reductants such as hydrogen and/or carbon monoxide, notably hydrogen. In one embodiment, the fluid stream is a liquid hydrocarbon stream containing dissolved hydrogen and/or carbon monoxide. In another embodiment, the fluid stream is a gaseous stream containing hydrogen and/or carbon monoxide, i.e. a reducing gas stream. Gas streams that may benefit from this process include synthesis gas streams from conventional steam reforming processes and/or partial oxidation processes, and synthesis gas streams from a coal gasifier, e.g. as part of a IGCC process, after gas washing and heat recovery (cooling) steps, and before the sour shift stage. Other streams that may benefit from the present invention include refinery vent streams, refinery cracker streams, blast furnace gases, reducing gases, particularly hydrogen-rich gas streams, ethylene-rich streams and liquid or gaseous hydrocarbon streams, e.g. naphtha, fed or recovered from hydrotreating processes, such as hydrodesulphurisation or hydrodenitrification.

In use, the sorbent may be placed in a sorption vessel and the fluid stream containing heavy metal is passed through it. Desirably, the sorbent is placed in the vessel as one or more fixed beds according to known methods. More than one bed may be employed and the beds may be the same or different in composition.

The invention is further described by reference to the following Examples.

EXAMPLE 1

Preparation of Sorbent

A mixture of a copper sulphide powder and a calcined, rehydratable alumina powder was prepared as follows:

| Component | Source | % wt |
|---|---|---|
| Copper sulphide (99%), | Eurolub | 33 |
| Calcined, rehydratable alumina | CP-5, BASF | 67 |

The properties of the calcined, rehydratable alumina powder were as follows:

| Chemical composition | (wt %) |
|---|---|
| Residual Moisture (dried a 250° C. for 30 minutes) | 2 |
| Total loss on ignition (250-1100° C.) | 7 |
| $SiO_2$ | <0.02 |
| $Fe_2O_3$ | <0.01 |
| $Na_2O$ | <0.4 |

Physical Properties

| | | |
|---|---|---|
| BET Surface area | 270 | $m^2/g$ |
| Packed bulk density | 38 | $lb/ft^3$ |
| Particle size distribution (average size) | 5 | µm |
| Particle size distribution (90 wt % <) | 12 | µm |
| XRD Phase | Amorphous | |

The powders were pre-mixed to ensure a homogenous mixture. Granules were then formed by nodulizing the mixture in a rotating pan while water (about 0.33 ml/g mixture) was sprayed onto the mixture as a fine mist. The water was found to be about 25 wt % of the mass of the shaped agglomerates before drying. This is significantly higher than the water content of the prior granulated sorbents which typically only comprise about 15 wt % water. Following granulation, the material was aged at 45° C. Following ageing, the material was dried in a fluid bed dryer at 105° C., to produce the sorbent.

The physical properties of the sorbent were determined, and are shown below compared to a sulphided copper sorbent prepared using basic copper carbonate, cement and clay binders, and an alumina trihydrate (ATH) support material, according to the method described in WO2009/101429.

The tapped bulk density (TBD) was measured by pouring approximately 500 mls of sorbent granules into a 500 ml plastic measuring cylinder and tapping it until a constant volume was achieved. The TBD was calculated by dividing the mass of sorbent by the tapped volume.

The drum tumbling loss (DrTL) was measured by rotating 100 g of sorbent through 1800 total revolutions at 60 rpm for 30 minutes according to the ASTM method D4058-96. The DrTL is reported as a percentage of the original mass.

The mean crush strength (MCS) was determined by crushing 25 granules of each sorbent using an Engineering Systems C53 machine to calculate mean crush strength based on a normal distribution.

| Example | Ageing time (h) | TBD (g cm$^{-3}$) | DrTL (%) | MCS (kgF) |
|---|---|---|---|---|
| 1(a) | 1 | 1.04 | 0.00 | 7.61 |
| 1(b) | 6 | 1.04 | n/a | 8.51 |
| 1(c) | 6 | 1.02 | 0.00 | 8.89 |
| 1(d) | 24 | 1.03 | n/a | 9.91 |
| 1(e) | 24 | 1.04 | 0.00 | 9.55 |
| Comparative | 12 | 0.99 | 2.20 | 1.48 |

The use of a calcined, rehydratable alumina provided a much stronger product when compared to the prior art material produced using mixed binders and aluminium trihydrate. The rate at which strength develops also occurs much more rapidly in the calcined, rehydratable alumina product when compared to the mixed binder product with strength achieved over 5 times higher following 1 hour of ageing.

The invention claimed is:

1. A method for preparing a sorbent comprising the steps of:
   (i) mixing a particulate copper sulphide material and a particulate calcined rehydratable aluminato to form a mixture,
   (ii) shaping the mixture, and
   (iii) drying the shaped mixture to form the sorbent.

2. A method according to claim 1 wherein the calcined rehydratable alumina comprises a calcined amorphous alumina or a transition alumina that is one or more of rho-alumina, chi-alumina, or pseudo gamma-alumina.

3. A method according to claim 1, wherein the particulate copper sulphide material (a) is manufactured by roasting copper or a copper compound with elemental sulphur, or (b) by precipitating copper sulphide from solution, sulphiding copper compounds using hydrogen sulphide, a mechano-chemical process that is mixing powdered copper metal with elemental sulphur under conditions that cause the elemental copper and elemental sulphur to react to form one or more copper sulphides.

4. A method according to claim 1, wherein the particulate copper sulphide material comprises one or more copper sulphides that is copper (II) sulphide, CuS, and/or substoichiometric copper sulphide of formula $Cu_{2-x}S$ where x is in a range of from 0 to 1.

5. A method according to claim 1, wherein the particulate copper sulphide material has an overall S:Cu atomic ratio of ≥0.8.

6. A method according to claim 1, wherein the particulate copper sulphide material is in the form of a powder with an average particle size, [D50], in the range of 5 µto 100 µm.

7. A method according to claim 1, wherein a copper content of the sorbent produced by the method is in a range of from 5% to 75% by weight expressed as CuS.

8. A method according to claim 1, wherein the particulate calcined rehydratable alumina is a powder with a $D_{50}$ particle size in a range of 1 to 100 µm.

9. A method according to claim 1, wherein a BET surface area of the calcined rehydratable alumina as determined by nitrogen adsorption is in a range of from 200 $m^2/g$ to 400.

10. A method according to claim 1, wherein the sorbent produced by the method consists essentially of the particulate copper sulphide material and the particulate calcined rehydratable alumina.

11. A method according to claim 1, wherein the shaping step comprises granulating the mixture in a granulator to produce granules of the sorbent.

12. A method according to claim 11 wherein the granulating is performed under a non-oxidising atmosphere.

13. A method according to claim 11, wherein the granules are aged for a time of from 0.5 hours to 8 hours before drying.

14. A method according to claim 1, wherein the sorbent is dried at a temperature up to 120° C. under a non-oxidising atmosphere.

15. A sorbent obtained by the method of claim 1.

16. A process for removing one or more heavy metals from a heavy metal-containing fluid stream by contacting the fluid stream with the sorbent according to claim 15.

17. A method according to claim 5, wherein the overall S:Cu atomic ratio is ≥0.9.

18. A method according to claim 7, wherein the copper content of the sorbent is in the range of 10 to 75% by weight expressed as CuS.

19. A method according to claim 8, wherein the particle size of the particulate calcined rehydratable alumina is in the range of from 1 µm to 20.

20. A method according to claim 9, wherein the BET surface area of the calcined rehydratable alumina as determined by nitrogen adsorption is in the range of from 250 $m^2/g$ to 300 $m^2/g$.

* * * * *

UNITED STATES PATENT AND TRADEMARK OFFICE
CERTIFICATE OF CORRECTION

PATENT NO. : 10,751,686 B2  
APPLICATION NO. : 15/578502  
DATED : August 25, 2020  
INVENTOR(S) : Matthew James Evans et al.

Page 1 of 1

It is certified that error appears in the above-identified patent and that said Letters Patent is hereby corrected as shown below:

In the Claims

Claim 1, Column 7, Line 5, delete "aluminato" and insert -- alumina --.

Signed and Sealed this  
Tenth Day of December, 2024

Katherine Kelly Vidal  
*Director of the United States Patent and Trademark Office*